US006585653B2

(12) United States Patent
Miller

(10) Patent No.: US 6,585,653 B2
(45) Date of Patent: Jul. 1, 2003

(54) MICRO-MACHINED ULTRASONIC TRANSDUCER (MUT) ARRAY

(75) Inventor: David G. Miller, North Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 7 days.

(21) Appl. No.: 09/919,536

(22) Filed: Jul. 31, 2001

(65) Prior Publication Data

US 2003/0028109 A1 Feb. 6, 2003

(51) Int. Cl.[7] ................................................ A61B 8/14
(52) U.S. Cl. ...................................................... 600/459
(58) Field of Search ................................ 600/407, 424, 600/437, 438, 439, 440–447, 458–471, 481; 128/916; 367/153, 154, 174, 181; 73/625, 626; 381/113, 116, 174, 190, 191; 29/25.35, 594; 604/4.01, 19, 93.1

(56) References Cited

U.S. PATENT DOCUMENTS 6,314,057 B1 * 11/2001 Solomon et al. ............ 367/174
6,381,197 B1 * 4/2002 Savord et al. .............. 367/178

* cited by examiner

*Primary Examiner*—Marvin M. Lateef
*Assistant Examiner*—Ali M. Imam
(74) *Attorney, Agent, or Firm*—John Vodopia

(57) ABSTRACT

An ultrasonic transducer array comprising individual transmit MUT elements and receive MUT elements includes the transmit MUT elements and the receive MUT elements distributed in two dimensions over the array. By using different MUT elements for transmit and receive operation, each MUT element can be independently optimized for either transmit operation or receive operation. Furthermore, by independently optimizing the MUT elements for either transmit or receive operation, the same bias voltage can be applied to the MUT elements, thereby simplifying the bias circuitry associated with the MUT transducer array. Alternatively, because the MUT elements are independently optimized for transmit and receive, different bias voltages can be applied to the transmit and receive elements, thus providing further optimization of the elements.

21 Claims, 5 Drawing Sheets

MICRO-MACHINED ULTRASONIC TRANSDUCER (MUT) ARRAY

TECHNICAL FIELD

The present invention relates generally to ultrasonic transducers, and, more particularly, to an efficient micro-machined ultrasonic transducer (MUT) array.

BACKGROUND OF THE INVENTION

Ultrasonic transducers have been available for quite some time and are particularly useful for non-invasive medical diagnostic imaging. Ultrasonic transducers are typically formed of either piezoelectric elements or of micro-machined ultrasonic transducer (MUT) elements. The piezoelectric elements typically are made of a piezoelectric ceramic such as lead-zirconate-titanate (PZT), with a plurality of elements being arranged to form a transducer. A MUT is formed using known semiconductor manufacturing techniques resulting in a capacitive ultrasonic transducer cell that comprises, in essence, a flexible membrane supported around its edges over a silicon substrate. By applying contact material, in the form of electrodes, to the membrane, or a portion of the membrane, and to the base of the cavity in the silicon substrate, and then applying appropriate voltage signals to the electrodes, the MUT may be energized such that an appropriate ultrasonic wave is produced. Similarly, when electrically biased, the membrane of the MUT may be used to receive ultrasonic signals by capturing reflected ultrasonic energy and transforming that energy into movement of the electrically biased membrane, which then generates a receive signal.

The ultrasonic transducer elements may be combined with control circuitry forming a transducer assembly, which is then further assembled into a housing possibly including additional control electronics, in the form of electronic circuit boards, the combination of which forms an ultrasonic probe. This ultrasonic probe, which may include various acoustic matching layers, backing layers, and de-matching layers may then be used to send and receive ultrasonic signals through body tissue.

In the past, MUT arrays were typically designed where each MUT element was a transceiver. In such an arrangement, each MUT element both produces a transmit pulse and receives acoustic energy. Unfortunately, the characteristics of a MUT element that make it a good transmitter of acoustic energy are not the same characteristics that make it a good receiver of acoustic energy. For example, during a transmit pulse, it is desirable for the MUT to provide a large power output. To accomplish this, a large membrane deflection, a large gap, high membrane stiffness, and high bias voltage are desired to produce the high pressure wave desired on transmit. In such a MUT, the cavity depth should be at least three times deeper than the static deflection of the membrane. Membrane deflection larger than approximately ⅓ of the cavity depth result in the collapse of the membrane against the cavity floor. The gap is defined as the distance between the membrane and the bottom of the cavity. A large gap results in a small capacitance and large imaginary impedance. Ideally a bias voltage is applied to deflect the membrane and reduce the gap to the minimum uncollapsed size.

Conversely, for a MUT to be a sensitive acoustic receiver, a small membrane deflection, a small gap, low membrane stiffness, and high bias voltage produce a sensitive acoustic receiver element. The small gap reduces the imaginary impedance and the soft membrane deflects easily when exposed to acoustic energy reflected from a target resulting in a high signal-to-noise ratio (SNR).

Therefore, it would be desirable to have a MUT array in which the individual MUT elements can be independently optimized for transmit and receive functionality.

SUMMARY

An ultrasonic transducer array comprising individual transmit MUT elements and receive MUT elements where the transmit MUT elements and the receive MUT elements are distributed in two dimensions over the transducer array is disclosed. By using different MUT elements for transmit and receive, each MUT element can be independently optimized for either transmit operation or receive operation. Furthermore, by independently optimizing the MUT elements for either transmit or receive operation, the same bias voltage can be applied to the MUT elements, thereby simplifying the bias circuitry associated with the MUT transducer array. Alternatively, because the MUT elements are independently optimized for transmit and receive, different bias voltages can be applied to the transmit and receive elements, thus providing further optimization of the elements.

Other systems, methods, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE INVENTION

The invention to be described hereafter is applicable to micro-machined ultrasonic transducer (MUT) elements connected to a substrate on which an integrated circuit (IC) can be formed.

Figure 1:
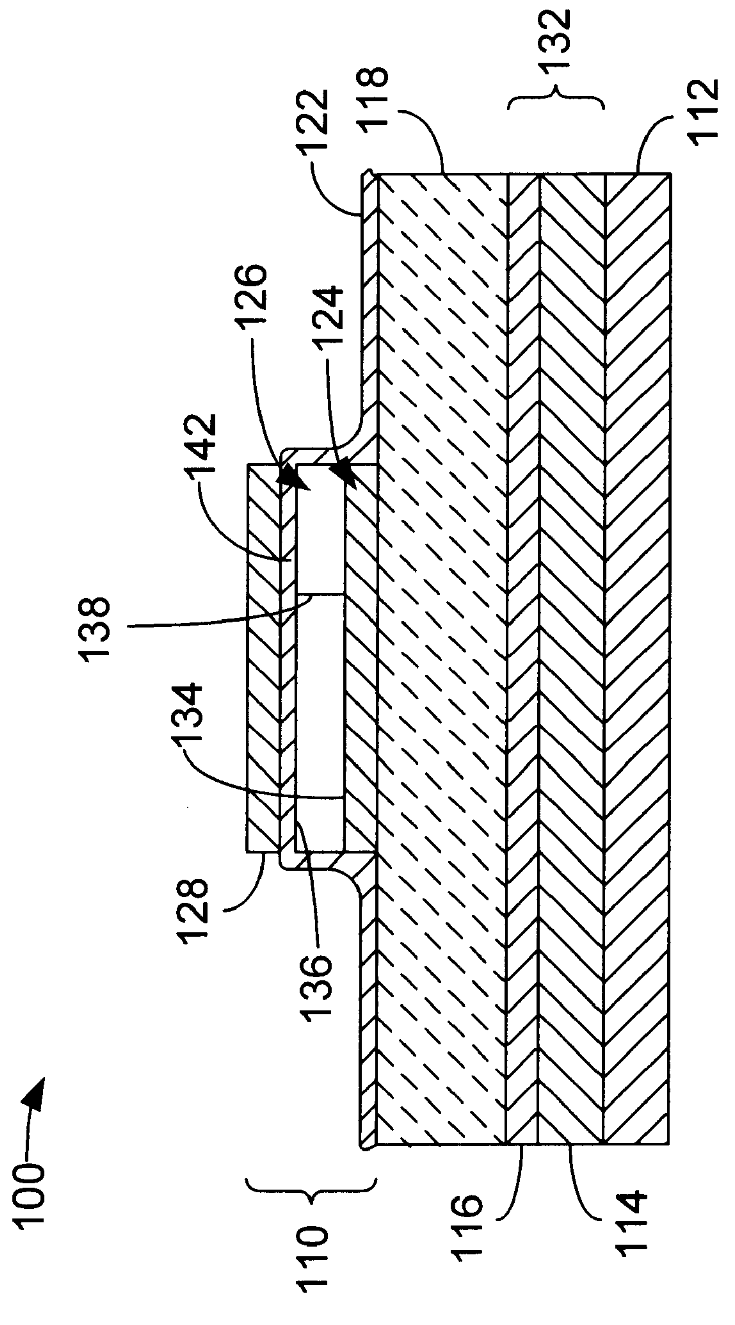
FIG. 1 is a cross-sectional schematic view of a micro-machined ultrasonic transducer (MUT) cell assembly under no electrical bias.

FIG. 1 is a cross-sectional schematic view of an exemplar micro-machined ultrasonic transducer (MUT) cell assembly 100 under no electrical bias. It should be mentioned that many techniques can be used to build MUT cells in many configurations, and the configuration shown in FIG. 1 (and in FIG. 2) is merely illustrative. The MUT cell assembly 100 generally includes an MUT cell 110 formed over an MUT substrate 118. The MUT cell assembly 100 may also include an integrated circuit (IC) assembly 132. The IC assembly 132 includes an IC substrate 114 over which is formed an integrated circuit 116. The IC substrate 114 can be any semiconductor substrate material, and in this embodiment is illustratively silicon (Si). In accordance with techniques known to those having ordinary skill in the art, an integrated circuit 116 is formed on the IC substrate 114. The integrated circuit 116 is shown exaggerated for illustrative purposes only. The IC assembly 132 is mounted on a printed circuit board or other substrate 112.

The MUT substrate 118 can also be formed using, for example, silicon, and includes an electrical contact 124 grown or deposited over one surface of the MUT substrate 118. A membrane 122, preferably constructed using silicon nitride, is applied over one of the exposed surfaces of the MUT substrate 118 and over the electrical contact 124 forming a cavity 126, sometimes referred to as a vacuum gap. The portion 142 of the membrane 122 that forms the cavity 126 is flexible. The cavity 126 defines a gap 138, which is the distance between the base of the cavity, referred to as the cavity floor 134 and the lower surface 136 of the flexible membrane portion 142.

An electrical contact 128 is applied over the flexible membrane portion 142 as shown in order to provide electrical connectivity to the cavity 126, which acts as a variable capacitor. The flexible membrane portion 142 is sufficiently flexible so that it can deflect in response to electrical signals applied through the electrical contacts 124 and 128, and in response to acoustic energy impinging on the flexible membrane portion 142. The circuitry that supplies electrical signals to the electrical contacts 124 and 128 to bias the MUT cell assembly 100 is omitted from the drawings for simplicity. However, those having ordinary skill in the art are familiar with such biasing circuitry.

The MUT substrate 118 can be joined to the integrated circuit 116 using, for example but not limited to, conductive vias (not shown) that extend from the electrical contact 124 through the MUT substrate 118 to the circuitry (not shown) on the integrated circuit 116. Such an attachment methodology is described in commonly assigned, copending U.S. patent application Ser. No. 09/919,470, filed on Jul. 31, 2001, (Attorney Docket No. US 010438), incorporated herein by reference.

Figure 2:
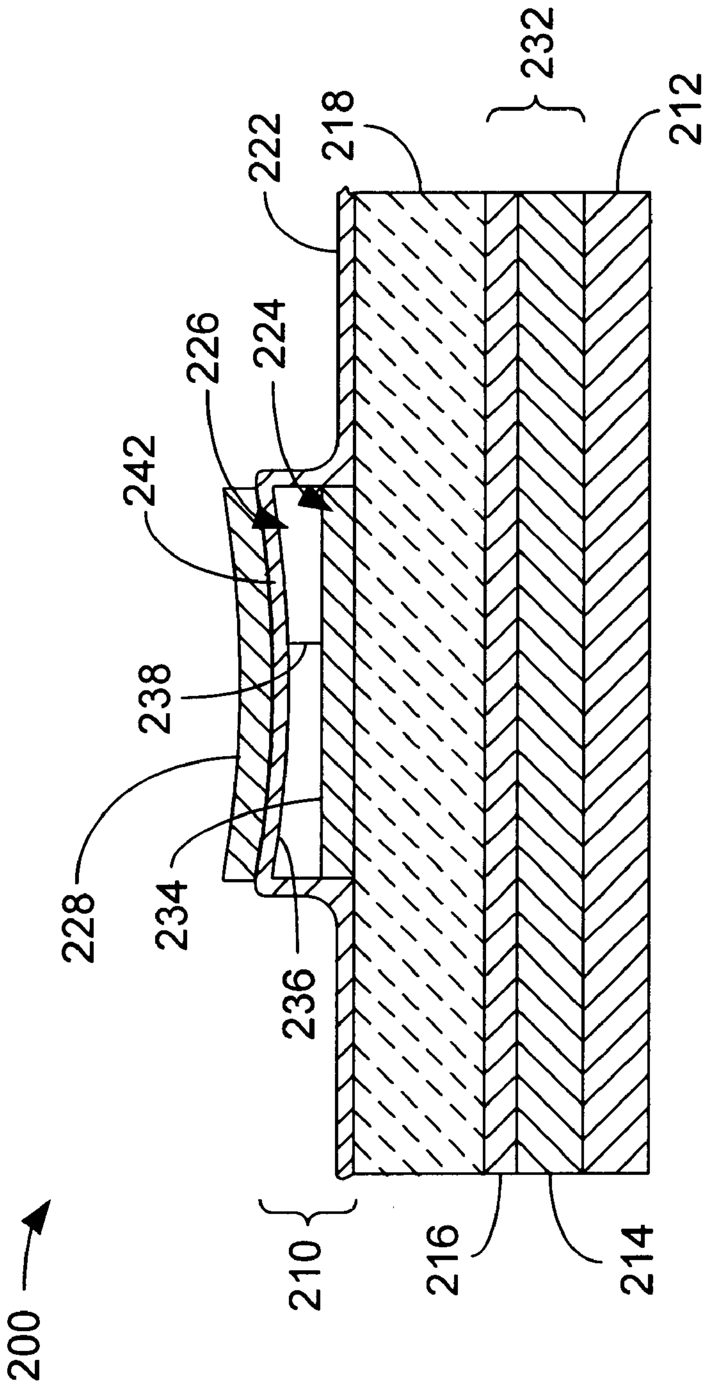
FIG. 2 is a cross-sectional schematic view of the MUT cell assembly of FIG. 1 under electrical bias.

FIG. 2 is a cross-sectional schematic view of the MUT cell assembly 100 of FIG. 1 under an electrical bias and now designated 200. The MUT cell assembly 200 generally includes an MUT cell 210 formed over an NUT substrate 213 and an IC assembly 232 including an IC substrate 214 over which is formed an integrated circuit 216, with the IC assembly 232 being mounted on a printed circuit board or other substrate 212. When an electrical potential is applied to the electrical contacts 224 and 228 of the MUT cell assembly 200, the flexible membrane portion 242 suspended over the cavity 226 deflects as shown. The deflection of the flexible membrane portion 242 reduces the size of the gap 233 between the surface 236 of the flexible membrane portion 242 and the floor 234 of the cavity 226. The acoustic properties of the MUT cell 210 can be altered by applying an electrical bias to the flexible membrane portion 242, thereby improving certain performance parameters. Furthermore, the physical properties of the MUT cell can be designed to define the acoustic performance of the MUT cell. Properties such as the depth and width of the cavity and the stiffness of the membrane can be changed to obtain the desired acoustic performance of the MUT cell. For example, for transmit NUT cells a large power output is desirable. To achieve a large power output, large membrane deflections are desired. Large deflections require a deep cavity 226. Cavity depths should be at least three times the static deflection of the flexible membrane portion 242. Deflections larger than one-third of the cavity depth result in the collapse of the flexible membrane portion 242 against the floor 234 of the cavity 226. A large cavity depth results in a large gap 238. A large gap 238 results in a small capacitance and large imaginary impedance, such that a large voltage only provides a small current flow. As shown in FIG. 2, the bias voltage applied deflects the flexible membrane portion 242 and reduces the gap 238 to a minimum uncollapsed size.

If the MUT cell assembly 200 in FIG. 2 is used as a receive element, a small gap 238 and a low stiffness membrane 222 are desired. A small gap 238 reduces the imaginary impedance and a low stiffness membrane 222 follows the deflection of the acoustic load experiencing the acoustic wave for a high signal-to-noise ratio. This combination improves the sensitivity of the MUT cell 210.

As mentioned above, the physical dimensions and characteristics of the MUT cell 210 can be changed depending upon the desired acoustic performance. In addition, the bias voltage applied to the MUT cell 210 can be used to alter the acoustic performance of the MUT cell 210. In one aspect of the invention, the MUT cells are optimized to use the same bias voltage for transmit and receive operation. In such an arrangement, the bias circuitry is simplified because only one bias voltage is supplied to each MUT cell, thereby simplifying the circuit traces for each MUT cell. Furthermore, the electrical bias circuitry can be tuned to optimize the performance of the MUT cells at different frequencies for different imaging situations. For example it may be desirable to transmit at a low frequency and receive at a high frequency.

Figure 3A:
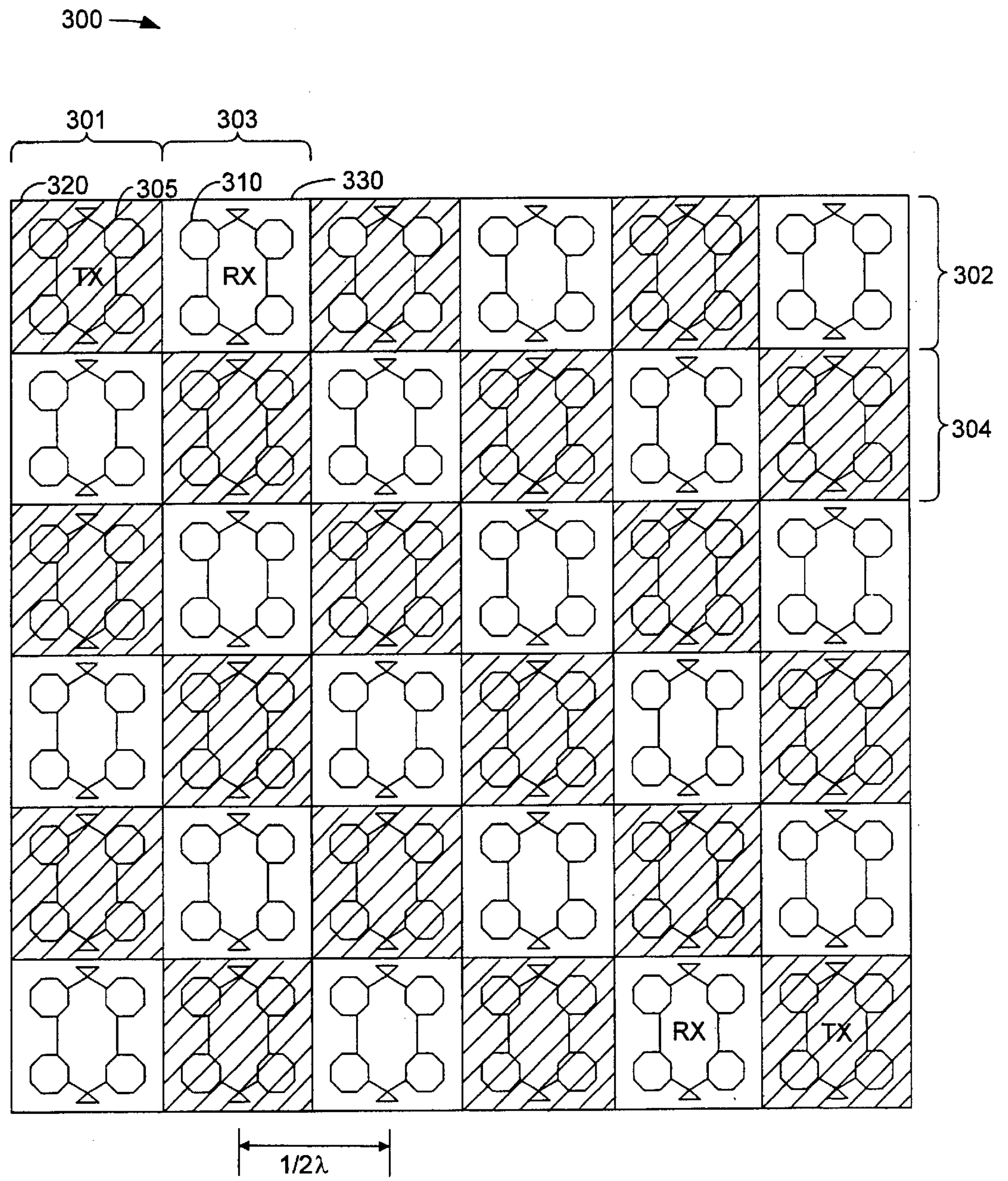
FIG. 3A is a plan view illustrating a MUT array constructed in accordance with an aspect of the invention and incorporating the MUT cells of FIGS. 1 and 2

FIG. 3A is a plan view illustrating a MUT array 300 constructed in accordance with an aspect of the invention and incorporating the MUT cells of FIGS. 1 and 2. The MUT array 300 includes a plurality of transmit MUT elements and receive MUT elements, exemplar ones of which are illustrated using reference numerals 320 and 330, respectively. Each transmit MUT element 320 and receive MUT element 330 includes a plurality of MUT cells, an exemplar one of which is illustrated using reference numeral 305 for the transmit MUT element 320 and reference numeral 310 for the receive MUT element 330. The MUT cells 305 and 310 correspond to the MUT cells 110 and 210 of FIGS. 1 and 2, respectively. Although illustrated using four octagonal MUT cells per element, other configurations and quantities of MUT cells per element are possible.

As illustrated in FIG. 3A, the transmit MUT elements 320 and the receive MUT elements 330 are arranged in an alternating pattern over the two dimensions of the MUT array 300. The transmit MUT elements 320 and the receive MUT elements 330 are arranged in columns and rows, exemplar columns being illustrated using reference numerals 301 and 303, and exemplar rows being illustrated using reference numerals 302 and 304. In the pattern illustrated in FIG. 3A, the transmit MUT elements 320 are non-adjacent the receive MUT elements 330. This arrangement results in a ½ wavelength (a wavelength is represented using the symbol λ), or less, pitch between transmit MUT elements 320 and receive MUT elements 330. The pitch is the centerline to centerline distance from one element to another. This ½λ pitch arrangement allows adequate sampling of the acoustic aperture, and also allows the ability to steer the ultrasonic beam along the principal axis in any direction. Those skilled in the art of phased array imaging systems will recognize the benefit of spacing the array elements on a ½ wavelength pitch to avoid the deleterious effects of grating lobes in the acoustic beam when steering the beam. By alternating the transmit MUT elements 320 and the receive MUT elements 330 in each column and row, each element in each column and row produces an ultrasonic beam contribution with an effective ½ wavelength pitch. This "checkerboard" pattern achieves the desired element pitch and also allows the ultrasonic beam to be steered in any direction. Thus, as shown in FIG. 3A, the transmit MUT elements 320 are arranged alongside and interspersed with the receive MUT elements 330 in the checkerboard pattern such that the transmit MUT elements 320 do not overlap the receive MUT elements 330 and vice versa. That is, as shown, there is no transmit MUT element 320 over or under a receive MUT element 330.

Furthermore, to meet the grating lobe requirement in the diagonal direction, the pitch in both directions can be reduced by the geometric relationship of 0.7 between of the hypotenuse and the sides of each element. Thus, any row or column of elements has a pitch of ½ wavelength or less for both transmitting elements and receiving elements. Such a configuration will be explained in greater detail below with respect to FIG. 3B. In this manner, the acoustic parameters of the transmit MUT element 320 and the receive MUT element 330 can be independently optimized, while maintaining a desirable narrow beamwidth. Although illustrated using a "checkerboard" pattern in FIG. 3A in which the MUT elements are distributed over the array in two dimensions, other configurations of transmit MUT elements 320 and receive MUT elements 330 are possible.

Furthermore, by having separate MUT elements for transmit and receive, independent biasing of the transmit and the receive MUT elements can easily be accomplished. In this manner, the MUT cells 305 in the transmit MUT elements 320 can be designed to provide the required large membrane deflection for maximum power, while the MUT cells 310 in the receive MUT elements 330 can be designed to have the smallest possible gap and the lowest possible membrane stiffness (and thus maximum sensitivity). Such receive MUT elements 330 can survive the reflected acoustic waves and can survive the medical imaging environment with the highest sensitivity and bandwidth.

Figure 3B:
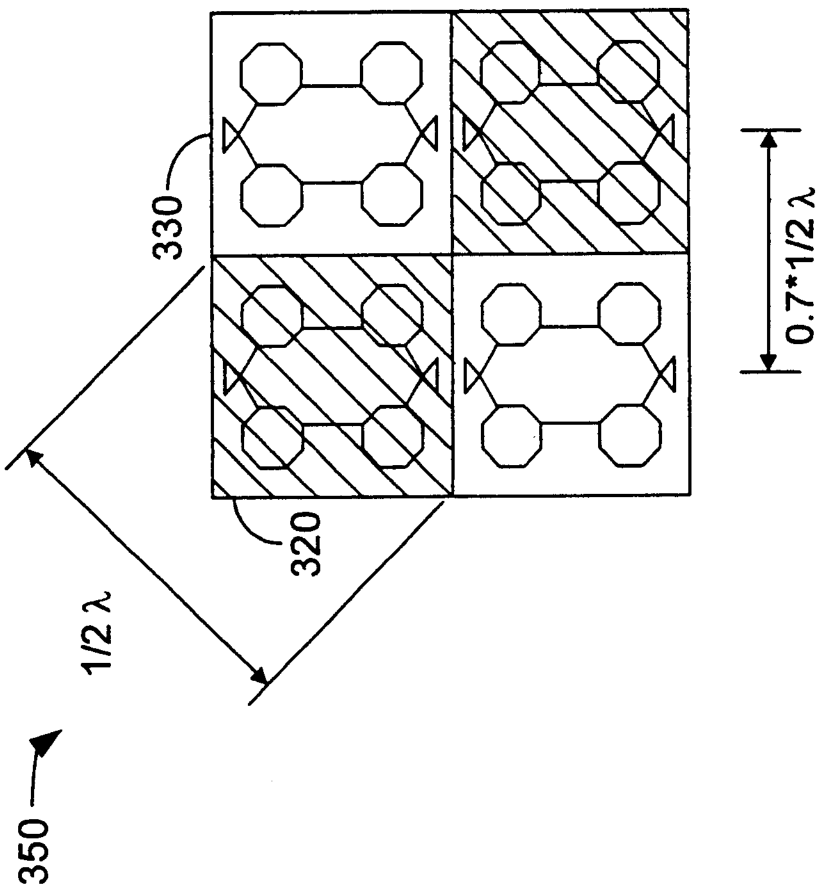
FIG. 3B is a plan view illustrating a portion of an alternative embodiment of the MUT array of FIG. 3A.

FIG. 3B is a plan view illustrating a portion 350 of an alternative embodiment of the MUT array of FIG. 3A. The array portion 350 includes a pair of transmit MUT elements 320 and a pair of receive MUT elements 330 having a pitch arranged so that the diagonal measurement of each element corresponds to a wavelength of $½\lambda$. As mentioned above, to avoid the deleterious effects of grating lobes in the acoustic beam when steering the beam not only in the principal axes, but in any direction, such as diagonally, the ½ wavelength pitch between the elements is reduced to approximately $0.7*½\lambda$. With the checkerboard combination described above, the element pitch of ½ wavelength is reduced to approximately $0.7*½\lambda$ as illustrated in FIG. 3B. When a $0.7*½\lambda$ element pitch is employed, the diagonal dimension of each of the elements shown in FIG. 3B corresponds to ½ wavelength. Furthermore, element pitch between $0.7*½\lambda$ and $½\lambda$ are possible.

Figure 4:
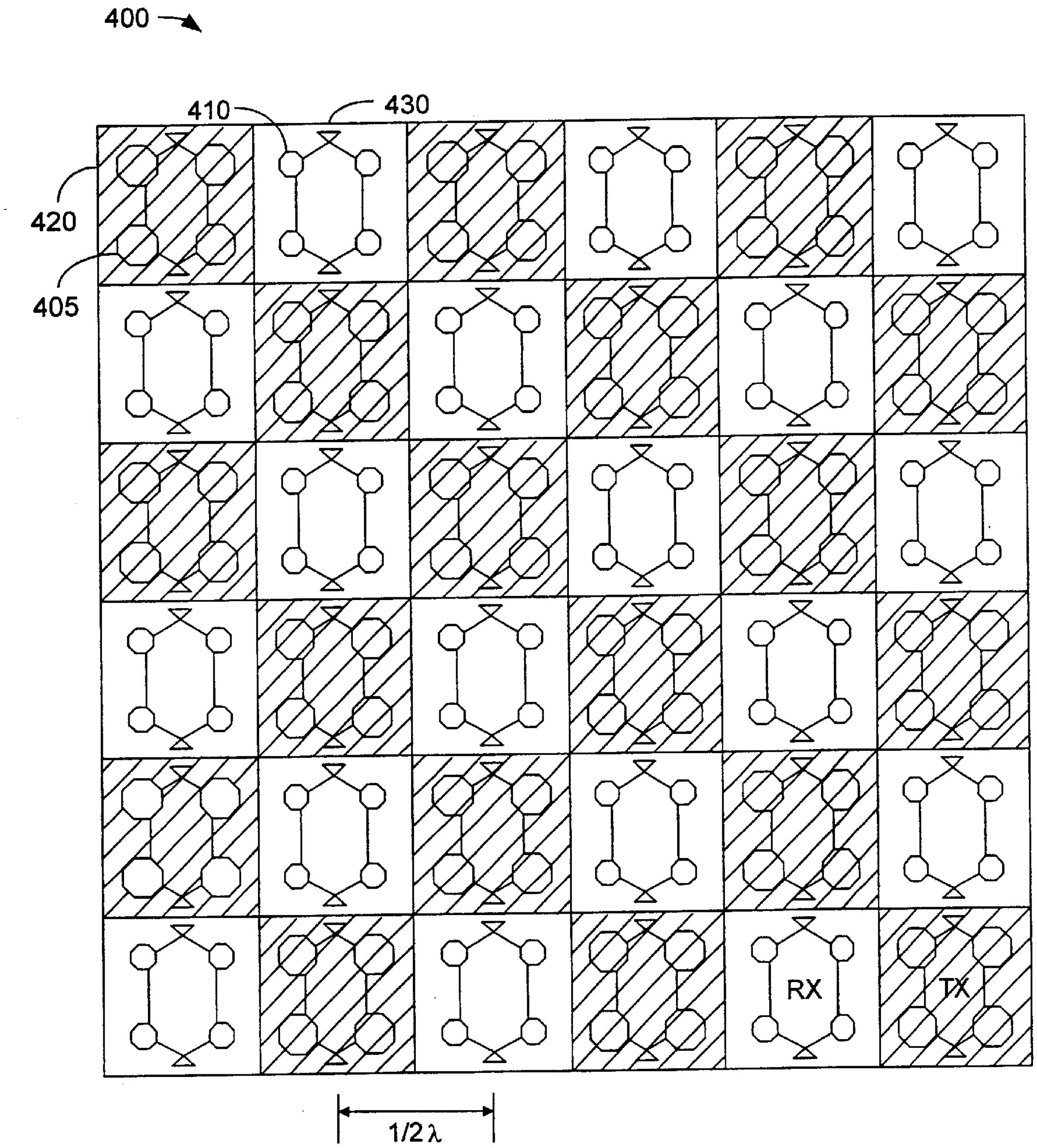
FIG. 4 is another alternative embodiment of the MUT array of FIG. 3A.

FIG. 4 is an alternative embodiment 400 of the transducer array 300 of FIG. 3A. The transducer array 400 includes separate transmit and receive MUT elements 420 and 430, respectively, but in the embodiment illustrated in FIG. 4, the receive MUT element 430 includes MUT cells 410 that are smaller in diameter than the MUT cells 405 in each transmit MUT element 420. Furthermore, the dimension of the MUT cell cavity (not shown in FIG. 4) in the MUT cells 410 can be different than the MUT cell cavity in the MUT cells 405. By altering the physical dimensions of the MUT cells 410, the receive performance of the transducer array 400 can be further improved.

In accordance with an aspect of the invention, the same bias voltage can be applied to the transmit MUT elements 420 and to the receive MUT elements 430. By altering the physical properties of the MUT cells 410 in the receive MUT element 430 with respect to the MUT cells 405 in the transmit MUT element 420, the acoustic performance of the respective receive and transmit MUT elements can be independently optimized. In this manner, and because the physical characteristics of the MUT cells 405 in the transmit MUT element 420 and the MUT cells 410 in the receive MUT element 430 are altered to independently optimize the respective acoustic performance of the transmit MUT element 420 and the receive MUT element 430, the same bias voltage can be applied to the transmit MUT element 420 and the receive MUT element 430. In this manner, the electrical biasing circuitry (not shown) can be simplified because the same bias voltage is applied to both transmit and receive MUT elements.

Alternatively, a different bias voltage can be applied to the transmit MUT elements and receive MUT elements shown above in FIGS. 3A, 3B and 4 in order to further independently optimize the acoustic performance of the respective transmit and receive elements.

It will be apparent to those skilled in the art that many modifications and variations may be made to the present invention, as set forth above, without departing substantially from the principles of the present invention. For example, the present invention can be used with piezoelectric ceramic and MUT transducer elements. Furthermore, the invention is applicable to different substrate materials including, for example, silicon and germanium. All such modifications and variations are intended to be included herein.

What is claimed is:

1. A micro-machined ultrasonic transducer (MUT) array, comprising:

a plurality of transmit MUT elements; and a plurality of receive MUT elements;

the plurality of transmit MUT elements and the plurality of receive MUT elements being distributed over the MUT array in two dimensions with the transmit MUT elements and receive MUT elements being arranged alongside one another in a non-overlapping relationship.

2. The transducer of claim 1, wherein the transmit MUT elements are non-adjacent the receive MUT elements.

3. The transducer of claim 1, wherein the transmit MUT elements and the receive MUT elements comprise a plurality of MUT cells and the MUT cells that comprise the transmit MUT elements are different in size than the MUT cells that comprise the receive MUT elements.

4. The transducer of claim 3, further comprising a membrane associated with each MUT cell, the membrane associated with an MUT cell of one of the transmit MUT elements being stiffer than a membrane associated with an MUT cell of one of the receive MUT elements.

5. The transducer of claim 4, wherein the membrane is suspended over a cavity, the membrane forming a gap between the membrane and a base of the cavity, and wherein the gap of an MUT cell of one of the transmit MUT elements is different than the gap of an MUT cell of one of the receive MUT elements.

6. The transducer of claim 5, wherein the gap is defined by the bias voltage applied to the MUT cell.

7. The transducer of claim 1, wherein the pitch of any one of the plurality of transmit MUT elements and any one of the plurality of receive MUT elements is equal to ½ wavelength of a transmit pulse associated with the transducer.

8. The transducer of claim 1, wherein the pitch of any one of the plurality of transmit MUT elements and any one of the plurality of receive MUT elements is equal to 0.7 times ½ wavelength of a transmit pulse associated with the transducer.

9. The transducer of claim 1, wherein the transmit MUT elements are non-adjacent the receive MUT elements in a third dimension perpendicular to the two dimensions.

10. A method for optimizing the acoustic performance of a micro-machined ultrasonic transducer (MUT) array, the method comprising the steps of:

optimizing a plurality of transmit MUT elements;

optimizing a plurality of receive MUT elements; and distributing the plurality of transmit MUT elements and the plurality of receive MUT elements over the MUT array in two dimensions with the transmit MUT elements and receive MUT elements being arranged alongside one another in a non-overlapping relationship.

11. The method of claim 10, wherein the distributing step distributes the transmit MUT elements non-adjacent the receive MUT elements.

12. The method of claim 10, wherein each transmit MUT element and each receive MUT element comprises a plurality of MUT cells and the MUT cells that comprise the transmit MUT elements are different in size than the MUT cells that comprise the receive MUT elements.

13. The method of claim 10, further comprising the steps of:

applying a first bias voltage to the transmit MUT elements; and applying a second bias voltage to the receive MUT elements.

14. The method of claim 13, further comprising the step of applying the same bias voltage to the transmit MUT elements and the receive MUT elements.

15. The method of claim 13, wherein further comprising the step of applying different bias voltages to the transmit MUT elements and the receive MUT elements.

16. The method of claim 10, further comprising the step of locating each of the plurality of transmit MUT elements and each of the plurality of receive MUT elements ½ wavelength of a transmit pulse associated with the transducer apart.

17. The method of claim 10, further comprising the step of locating each of the plurality of transmit MUT elements and each of the plurality of receive MUT elements 0.7 times ½ wavelength of a transmit pulse associated with the transducer apart.

18. The method of claim 10, wherein the distributing step distributes the transmit MUT elements non-adjacent the receive MUT elements in a third dimension perpendicular to the two dimensions.

19. A micro-machined ultrasonic transducer (MUT) array, comprising:

a plurality of transmit MUT elements; and a plurality of receive MUT elements;

the plurality of transmit MUT elements and the plurality of receive MUT elements being distributed within a distance corresponding to ½ wavelength of a transmit pulse associated with the MUT array with the transmit MUT elements and receive MUT elements being arranged alongside one another in a non-overlapping relationship.

20. The transducer of claim 19, wherein the plurality of transmit MUT elements and the plurality of receive MUT elements are distributed within a distance corresponding to 0.7 times ½ wavelength.

21. A micro-machined ultrasonic transducer (MUT) array, comprising:

a plurality of MUT elements arranged in columns and rows in a planar array, said plurality of MUT elements including transmit MUT elements and receive MUT elements, said transmit MUT elements and said receive MUT elements being arranged such that each column and each row includes at least one transmit MUT element and at least one receive MUT element and in each column and in each row, any one of the transmit MUT elements is adjacent to only one or more of the receive MUT elements and any one of the receive MUT elements is adjacent to only one or more of the transmit MUT elements.

* * * * *